US00PP12339P2

(12) United States Plant Patent
Heims

(10) Patent No.: US PP12,339 P2
(45) Date of Patent: Jan. 8, 2002

(54) PULMONARIA PLANT NAMED 'EMERALD ISLES'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/629,111

(22) Filed: Jul. 31, 2000

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Pulmonaria plant characterized by a unique combination of emerald green spots and pink flowers turning to blue.

1 Drawing Sheet

The present invention relates to a new and distinct hybrid of Pulmonaria, of the family Boraginaceae, which originated as an open-pollinated cross between Pulmonaria 'Victorian Brooch' U.S. Plant Pat. No. 11,234 (seed parent) and an unknown pollen parent. This is known to be an outcross because Pulmonaria does not normally self-pollinate. Due to the fact that the instant plant and parent plants are the result of crosses between several different Pulmonaria species, no species designations are given.

This hybrid was selected from a large selection of seedlings. The seed parent was retained to observe habit and to compare with the instant plant. The new variety has been reproduced only by asexual propagation (division and tissue culture). Each of the progeny exhibits identical characteristics to the original plant.

This plant is characterized by the following:

1. Foliage with emerald green spots instead of silver.
2. Pink flowers turning to blue.

Asexual propagation by division and tissue culture as done in Canby, Oreg., shows that the foregoing characteristics and distinctions come true to form and are established and transmitted through succeeding propagations.

BRIEF DESCRIPTION OF THE DRAWING

The drawing shows Pulmonaria 'Emerald Isles' in Canby, Oreg.

DETAILED PLANT DESCRIPTION

The following is a detailed description of the new Pulmonaria hybrid based on observations of 1.5-year old specimens grown in a gallon size pot in Canby, Oreg. The color descriptions are all based on The *Royal Horticultural Society Colour Chart*. The present invention has not been evaluated under all possible environmental conditions. The phenotype may vary with variations in environment without a change in the genotype of the plant.

Plant:
- *Type.*—Herbaceous perennial. Retains foliage in USDA zones 6 and above. Dies down to the ground in USDA zones 4–5.
- *Height.*—18 cm.
- *Width.*—38 cm.

Leaf:
- *Type.*—Simple.
- *Shape.*—Ovate to oblong.
- *Length.*—10 cm.
- *Width.*—5.5 cm.
- *Petiole length.*—11 cm.
- *Margins.*—Entire, ciliolate. Slight undulation.
- *Apex.*—Broadly acute.
- *Base.*—Attenuate to rounded.
- *Leaf texture.*—Velutinous to setose.
- *Petiole texture.*—Scurfy.
- *Leaf arrangement.*—Rosette.
- *Venation.*—Reticulate.

Flower bud:
- *Size.*—About 2 cm. deep and 0.6 cm wide.
- *Shape.*—Ovoid with a tube.

Flower:
- *Type.*—Complete. Perfect.
- *Shape.*—Funnelform.
- *Size.*—1.25–1.5 cm. wide.
- *Corolla.*—5 fused petals with rounded lobes.
- *Calyx.*—5 fused sepals, campanulate, parted ⅔ to base, hispid and glandular hairs, and 1.6 cm. deep.
- *Pistil.*—Exerted or pin type.
- *Ovary position.*—Partially inferior.
- *Carpel number.*—4.
- *Stamen number.*—5, in the tube.
- *Inflorescence type.*—Forked cymes.
- *Peduncle width.*—3–4 mm at its widest.
- *Peduncle texture.*—Setulose.
- *Blooming height.*—To 15 cm.
- *Bloom period.*—Late February to early May in Canby, Oreg.
- *Fragrance.*—None.

Seed:
- *Type.*—4 smooth nutlets, black and shiny, typical of the genus.
- *Fertility.*—Fertile.

Habit: Clumping.

Disease: Minor susceptibility to powdery mildew observed on plants grown in sub-optimal conditions.

Hardiness: USDA zones 4–9.

Color Characteristics

Foliage:
- *Upper surface.*—RHS 137A Green Group.

*Upper surface, spots.*—RHS 138B Green Group.

*Lower surface.*—RHS 148C–D Yellow-Green Group.

Flower:

*Bud.*—RHS 63A Red-Purple Group.

*Corolla.*—RHS 63A Red-Purple Group turning to RHS 93B Violet-Blue Group.

*Calyx.*—RHS 137B Green Group.

*Pollen.*—RHS 155B White Group.

*Seed.*—RHS 202A Black Group.

Peduncle: RHS 143B Green Group.

DESCRIPTION OF PARENT PLANTS

The instant plant resulted from a cross between Pulmonaria 'Victorian Brooch' U.S. Plant Pat. No. 11,234 (seed parent) and an unknown pollen parent. Pulmonaria 'Victorian Brooch', as described in U.S. Plant Pat No. 11,234, has very large flowers on a compact scape and distinctive spotted, ovate foliage. The instant plant differs from Pulmonaria 'Victorian Brooch' in having green spotting instead of silver and pink flowers that turn to blue.

Compared to Pulmonaria 'High Contrast' (U.S. Plant patent application Ser. No. 09/628,782), the instant plant has a smaller habit and lighter green leaves.

Compared to Pulmonaria 'Dark Vader' (U.S. Plant patent application Ser. No. 09/628,783), the instant plant has a smaller habit, lighter green and more silvered leaves, and the style is a thrum (included in the tube) rather than a pin type (exerted).

I claim:

1. A new and distinct hybrid of Pulmonaria plant substantially as shown and described, characterized by a unique combination of emerald green spots and pink flowers turning to blue.

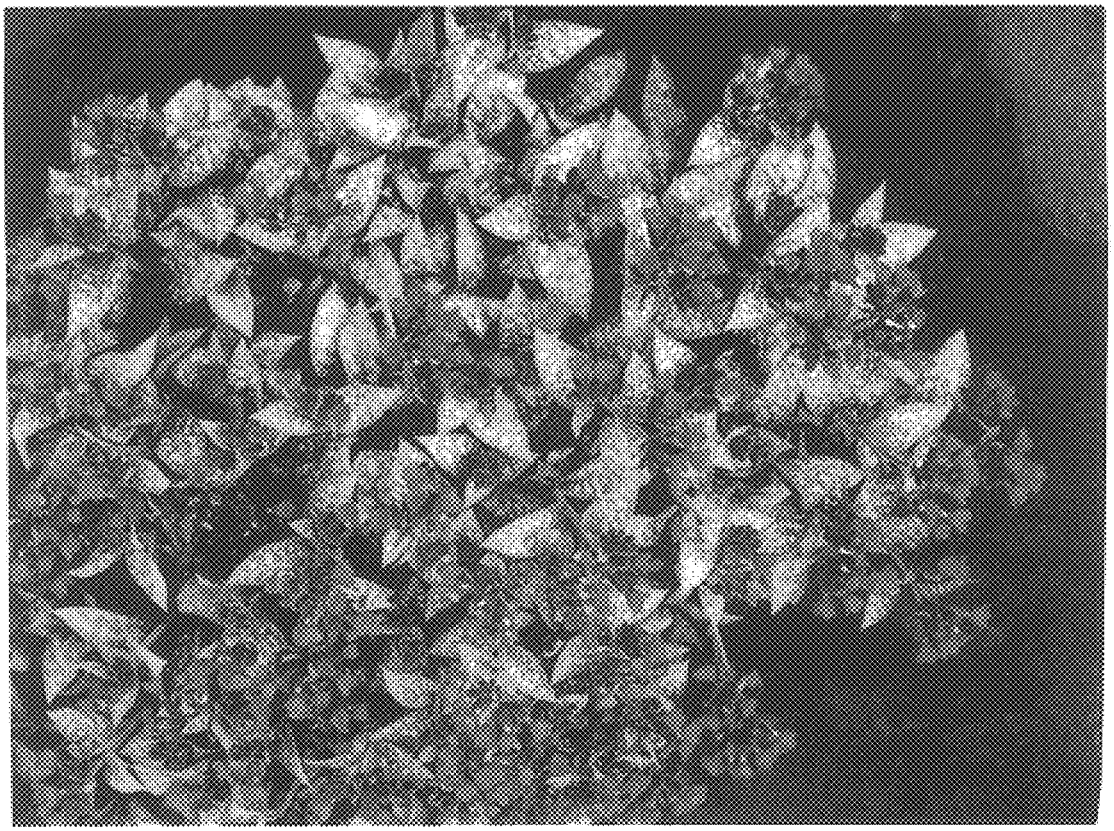

* * * * *